Figure 3:
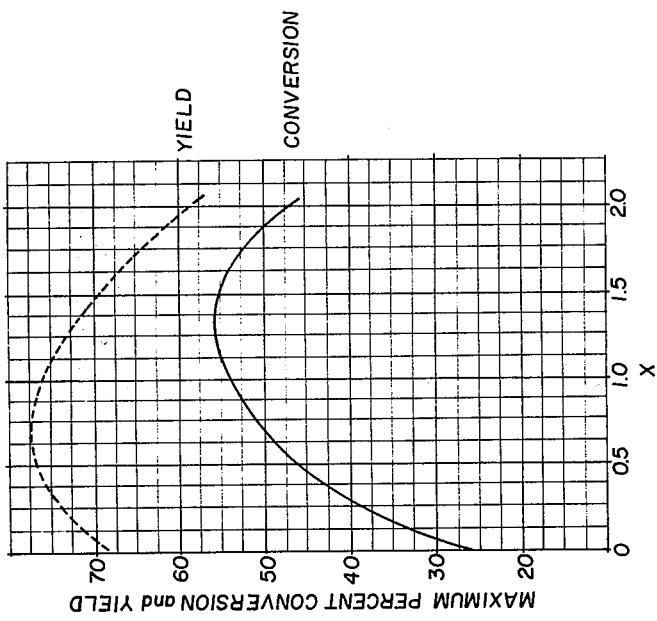

United States Patent [19]

Watkins

[11] 3,975,301

[45] Aug. 17, 1976

[54] DEHYDROGENATION CATALYST CONSISTING OF THE CALCINED RESIDUE OF FERRIC PHOSPHATE AND LEAD PHOSPHATE

[75] Inventor: Windell C. Watkins, Longview, Tex.

[73] Assignee: Eastman Kodak Company, Rochester, N.Y.

[22] Filed: Aug. 20, 1974

[21] Appl. No.: 498,885

Related U.S. Application Data

[62] Division of Ser. No. 409,823, Oct. 26, 1973, Pat. No. 3,855,279.

[52] U.S. Cl. .............................................. 252/437
[51] Int. Cl.$^2$......................................... B01J 27/14
[58] Field of Search ................................... 252/437

[56] References Cited
UNITED STATES PATENTS

| | | | |
|---|---|---|---|
| 2,336,600 | 12/1943 | Fawcett | 252/437 |
| 3,634,494 | 1/1972 | Tsu | 252/437 |
| 3,828,101 | 8/1974 | Miklas | 252/437 |

*Primary Examiner*—Patrick P. Garvin
*Assistant Examiner*—John P. Sheehan
*Attorney, Agent, or Firm*—Edward R. Weber; Daniel B. Reece, III

[57] ABSTRACT

Lower aliphatic acids, e.g., isobutyric acid, and esters, e.g., methyl isobutyrate, are dehydrogenated in the presence of oxygen and a solid heterogeneous dehydrogenation catalyst at temperatures in the range of from about 250°C. to about 600°C. The catalyst is the calcined residue of the mixed phosphates of iron and lead.

13 Claims, 3 Drawing Figures

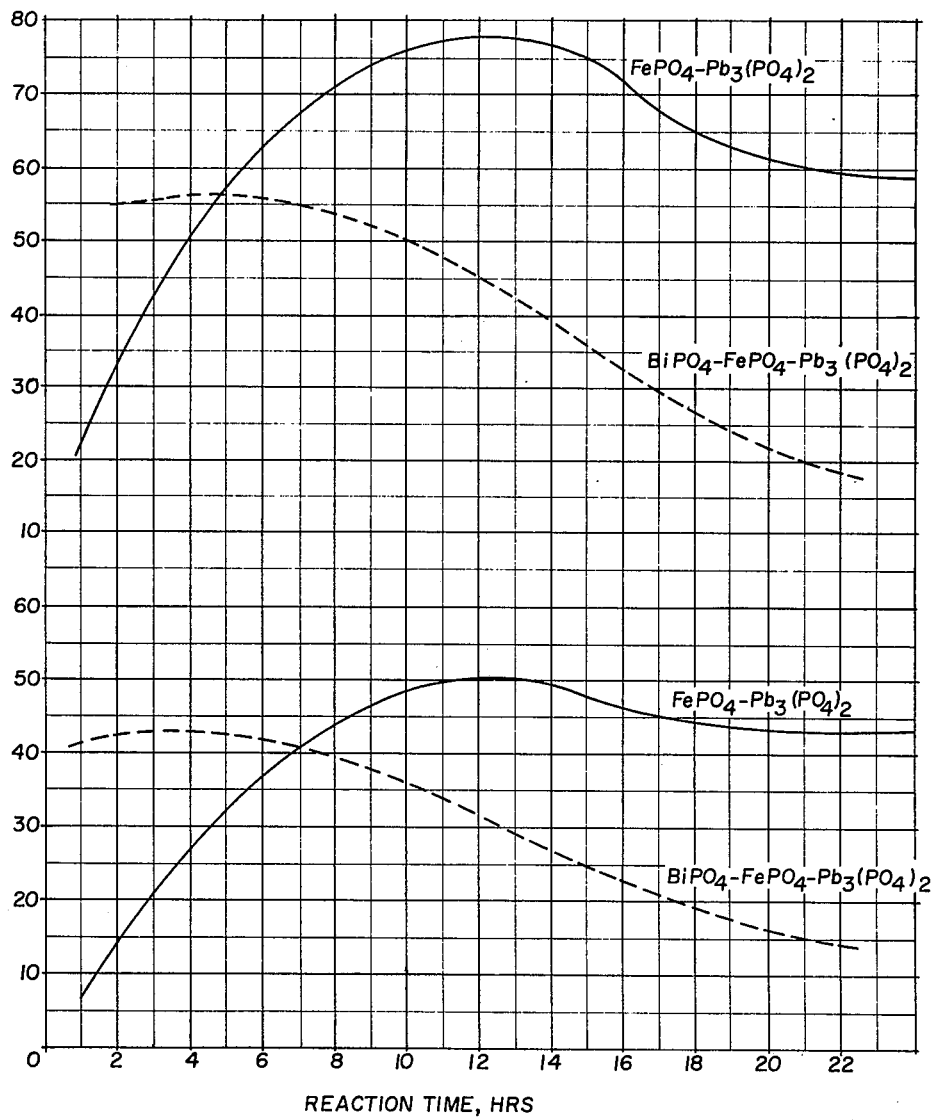

EFFECT of COMPOSITION of $FePO_4$-$Pb_3(PO_4)_2$ CATALYST on ACTIVITY
MAXIMUM CONVERSION and YIELD vs X in 1Fe:XPb
TEMP.=450°C, $H_2O$/IBA=13, $O_2$/IBA=0.77

EFFECT of $H_2O$/IBA MOLE RATIO on CONVERSION and YIELD
$FePO_4$-$Pb_3(PO_4)_2$ CATALYST
TEMP.=450°C  $O_2$/IBA=0.76

DEHYDROGENATION CATALYST CONSISTING OF THE CALCINED RESIDUE OF FERRIC PHOSPHATE AND LEAD PHOSPHATE

This is a division of application Ser. No. 409,823 filed Oct. 26, 1973, now U.S. Pat. No. 3,855,279.

This invention relates to the synthesis of unsaturated lower aliphatic acids and esters of such acids by catalytic oxidative dehydrogenation of the corresponding saturated acids and esters.

The catalytic dehydrogenation of the lower alkane acids and their esters has been described in prior art. One known process has been carried out using a metal oxide catalyst but with no molecular oxygen present during the dehydrogenation. In such a process the catalyst is rapidly deactivated and requires frequent regeneration. Such a process operates with relatively low conversion per pass which increases operating costs and size of required equipment. See data presented in *Industrial and Engineering Chemical Products, Research and Development*, Vol. II, p. 287 (1963) and U.S. Pat. No. 2,945,057. In another known process, dehydrogenation of lower alkane acids and their esters has been carried out with a metal oxidizing agent, but again without the presence of molecular oxygen. In that process the metal sulfide acts as a mild oxidizer which is chemically reduced and requires frequent regeneration. See U.S. Pat. No. 3,370,087.

More recently, U.S. Pat. No. 3,634,494 describes a process wherein the catalyst consists of the calcined mixed phosphates of iron, bismuth, and, in some embodiments, lead. The catalyst of U.S. Pat. No. 3,634,494 gives attractive conversions and yields; however it suffers from a relatively short catalyst life. In addition, the catalyst cannot be satisfactorily regenerated to its original active state. Therefore, the process of U.S. Pat. No. 3,634,494 loses much of its attractiveness.

Of the many catalytic systems described in the literature, including those detailed above, none have all the desirable properties of good catalysts. Among the criteria by which a catalyst is judged acceptable are high conversion and yield, long catalyst life and ease of regeneration to the original activity.

Accordingly, one of the objects of the instant invention is to provide an improved catalyst giving good conversions and yields and having a long catalyst life.

Another object of the instant invention is to provide a catalyst which can be easily regenerated to its original activity.

Yet another object of the invention is to provide a catalyst which can be simply prepared from readily available, inexpensive materials.

These and other objects and advantages of the instant invention will become quite clear from the following description, drawings and the appended claims.

In the accompanying drawings,

FIG. 1 presents a graphical comparison of conversion and yield versus time for the catalyst of the instant invention and the catalyst of prior art patent U.S. Pat. No. 3,634,494.

Figure 2:
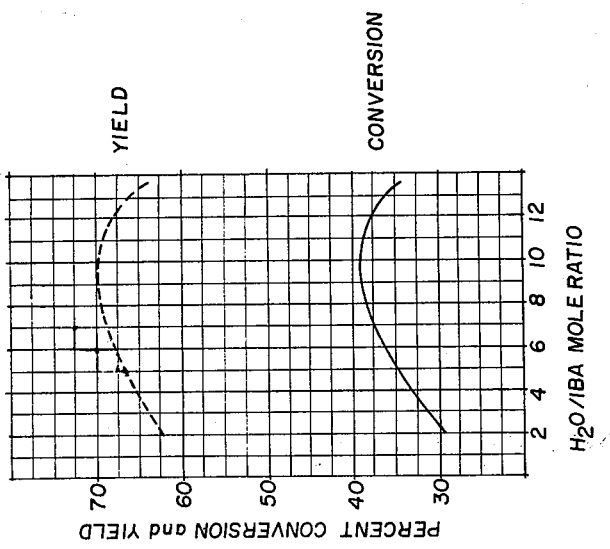

FIG. 2 depicts the effect of variations in the ratio of $H_2O$ to feed material on conversion and yields obtained with a catalyst prepared in accordance with the instant invention; and FIG. 3 illustrates the effect of variations in the composition of the catalyst, i.e., the ratio of Pb to Fe on conversion and yield.

In accordance with the instant invention, a lower aliphatic acid or an ester thereof having the formula

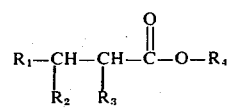

wherein $R_1$, $R_2$, $R_3$ and $R_4$ are selected from the group consisting of hydrogen and lower alkyl groups containing 1–4 carbon atoms, is selectively dehydrogenated to the $\alpha,\beta$-unsaturated equivalent acid or ester by contacting a gas-feed mixture comprising oxygen and the organic compound with an oxydehydrogenation catalyst comprising iron and lead combined with phosphorus and oxygen, which catalyst can be described nominally as the residue from the calcined phosphates of the metals. Dehydrogenation occurs at temperatures of from about 250°C. to about 600°C., preferably from about 350°C. to about 500°C. For economy, a preferred pressure for the oxydehydrogenation is about atmospheric pressure, but the process may be carried out at pressures in the range of from about 0.3 atmosphere to about 10 atmospheres or higher if desired. Water, present as steam during the reaction, is found to improve the results of the process. The ratio of oxygen to saturated acid or ester in the feed mixture is preferably about 0.1 to about 6 gram atoms of oxygen per mole of compound to be dehydrogenated. If desired, the oxygen may be diluted with an inert gas such as helium, nitrogen, argon, etc. A preferred source of oxygen is air.

The catalyst of the instant invention is the calcined residue of a mixture of ferric phosphate and lead phosphate wherein the atomic ratio of the metals is defined by 1 Fe/$x$ Pb where $x$ is from about 0.1 to about 10. A preferred range for $x$ is from about 0.5 to about 1.5.

The catalyst may be prepared by any of numerous methods suitable to yield the desired mixture of phosphates. In a particularly simple method, ferric nitrate enneahydrate and the lead nitrate are dissolved in water and precipitated by the addition of aqueous dibasic ammonium phosphate. The catalyst is washed, dried, broken into particles of the desired size and calcined at a temperature of from about 400°C. to about 600°C. Optionally, the catalyst may be pressed into tablets prior to calcining to get a more convenient catalyst shape.

In a preferred embodiment, the iron-lead phosphate catalyst is obtained by precipitating the iron-lead phosphates from an aqueous solution of their nitrates by the addition of a dibasic ammonium phosphate solution. This yields a final solution pH of approximately 5.5.

It has been found that the calcined catalyst contains more phosphorus than would be theoretically expected. A typical catalyst, considered as a mixture of iron phosphate plus lead phosphate, would have a theoretical iron:lead:phosphorus atomic ratio of 1:0.6:1.4. By analysis, the ratio is found to be 1:0.6:1.7–2.3. The phosphorus present in excess of the 1.4 ratio may be present as $P_2O_5$, $H_4P_2O_7$, polyphosphoric acid or it may be associated with the metals in some unknown way.

The catalyst may also be prepared by adding phosphoric acid to an aqueous solution of iron and lead nitrates and adjusting the pH to about 5.5 by the addition of ammonium hydroxide. Using sodium hydroxide instead of $NH_4OH$ results in a catalyst containing sodium which has a very low activity. Other bases, such as methylamine, ethylamine, pyridine, etc., may also be used but are expensive and thus not commercially attractive.

The pH of the iron-lead nitrate solution should be near 2.0 so that when the $(NH_4)_2HPO_4$ is added, a final pH of 5–7 is obtained. Adjusting the pH of the iron-lead nitrate solution to a higher value prior to the addition of phosphate [necessary if $(NH_4)H_2PO_4$ is to be used and a final pH of 5–7 is desired] causes iron and lead to precipitate as the hydroxides.

Precipitating the iron-lead with $(NH_4)H_2PO_4$ followed by the addition of $NH_4OH$ to adjust the pH is equally ineffective. Changing the pH after the precipitate is formed has little or no effect on the catalyst activity, i.e., the activity remains low.

Preferably the pH of the solution of salts of iron and lead is from about 0.5 to about 4.0 (more preferably from about 2 to about 2.5) prior to precipitation, and from about 5 to about 7 following precipitation.

The catalyst may be used in its calcined solid form without support, or it may be used on a catalyst support such as silica, silica-alumina, or silicon-carbide. The process in which the subject catalyst is used involves the passage of a mixture of the feed-saturated acid or ester, water and air over the catalyst contained in a fixed bed. The temperature of the catalyst bed is maintained at from about 250°C. to about 600°C., a preferred range being from about 350°C. to about 500°C., and a more preferred range being from about 400°C. to about 450°C.

In practice, higher conversions and yields are obtained when several catalyst zones are used with mixing zones separating them. The total volume of air is added in portions above each catalyst zone. Most of the work with the catalyst of the invention has been carried out in a reactor with two catalyst zones and two air inlet points. The data obtained in a two-stage reactor can be related to a multistage reactor as has been shown when a three-stage reactor was used in a bench-scale pilot plant to determine catalyst life, scale-up factors, etc.

The reactor effluent is cooled to condense a mixture composed mainly of water, unreacted feed acid or ester and product $\alpha,\beta$-unsaturated acid or ester. The presence of water in the reactor facilitates the oxidative dehydrogenation reaction but its role in the reaction mechanism is unknown. Optimum concentration of water usually will be in the range of 0.5 to about 20 moles water per mole of feed acid or ester. However, up to about 40 moles of water per mole of acid or ester may be used.

The catalyst of the prior art U.S. Pat. No. 3,634,494 is a mixture of the phosphates of bismuth, iron and lead with the metals present in an atomic ratio of 2:1:0.6, respectively. When this catalyst is prepared and used in a two-stage reactor, conversion and yields of isobutyric to methacrylic acid are in the range of 35 ± 5 percent and 45 ± 5 percent, respectively. Under identical conditions, the catalyst of the instant invention, i.e., a mixture of phosphates of iron and lead with the metals present in an atomic ratio of 1:0.6, gives conversions and yields to methacrylic acid of 50 ± 5 percent and 75 to 95 percent, respectively. Thus, the catalyst of the instant invention is a great improvement over the catalyst of the prior art. The prior art also teaches that bismuth is a necessary ingredient in the catalyst. Thus, it was quite surprising that a better catalyst could be obtained by the elimination of bismuth. The catalyst of the instant invention is a much simpler catalyst than the catalyst of U.S. Pat. No. 3,634,494 inasmuch as it contains only two metal components. The instant catalyst is also less expensive since the expensive component, bismuth nitrate, is not required. Not only is the catalyst of the instant invention more active than the prior art bismuth/iron/lead catalyst but it also has a longer life and is capable of regeneration through several cycles. Regeneration is obtained by passing air through the catalyst bed at about 450°C. to about 550°C. without the necessity of removing the catalyst from the process reactor. When the catalyst is regenerated in this manner, its activity readily returns to the original high level. In contrast to this, the three-metal catalyst of U.S. Pat. No. 3,634,494 cannot be satisfactorily regenerated.

This invention is further illustrated by the following examples which are set forth for purposes of illustration only and should not be construed as limiting the invention in any matter.

The reactor used in Examples 1–9 is a one-inch by 30-inch Vycor tube with a thermowell in the center extending the length of the tube. At the top of the reactor are provisions for feeding air, isobutyric acid, and water. Another air inlet is positioned 10 inches from the bottom of the tube. Isobutyric acid and water are metered into the reactor through a calibrated pump. The rate of isobutyric acid addition is 40 milliliters per hour and water is fed at such a rate as to obtain the desired water to isobutyric acid mole ratio. Air is introduced into the reactor at two feed points through rotameters at such rates as to obtain the desired oxygen to isobutyric acid mole ratio. Thirty-one percent of the air is fed to the top of the reactor and 69 percent is fed in the center. Two 20-milliliter catalyst beds are positioned in the reactor such that the central air inlet is between them. The volume between the catalyst beds and above the upper bed is filled with Vycor chips. The reactor is placed in an electric furnace and the temperature of the reactor is measured and controlled by means of thermocouples in the thermowell which are attached to temperature controllers.

The reactor effluent is condensed and collected. Every two hours the effluent is analyzed by gas chromatography using an internal standard and the conversion and yield are calculated by the following equations.

$$\% \text{ conversion} = \frac{\text{moles MAA in product}}{\text{moles IBA fed}} \times 100$$

$$\% \text{ yield} = \frac{\text{moles MAA in product}}{\text{moles IBA fed} - \text{moles IBA in product}} \times 100$$

where

MAA = methacrylic acid
IBA = isobutyric acid

After the reactor has run for eight hours, the conversions and yields for all the samples are averaged and reported. The selectivity shown in U.S. Pat. No. 3,634,494 is equivalent to the percent yield defined above. For comparison, the conversion calculated by the method used in U.S. Pat. No. 3,634,494 is also reported. This conversion, which I prefer to call consumption, is defined by the following equation.

$$\% \text{ consumption} = \frac{\text{moles IBA fed} - \text{moles IBA in product}}{\text{moles IBA fed}} \times 100$$

Also calculated for each run are water to isobutyric acid mole ratio, oxygen to isobutyric acid mole ratio, and contact time. Contact time ($\theta$) is defined by the following equation.

$$\theta = \frac{V_c \cdot 273}{V_g \cdot (273 + T)}$$

where
- $V_c$ = volume of catalyst in milliliters
- $V_g$ = total gas flow rate at STP in milliliters per second
- $T$ = reactor temperature in °C.

EXAMPLE 1

This example shows the high activity of the catalyst of this invention. Also, the ability to regenerate this catalyst is demonstrated.

To a solution of 323 grams ferric nitrate enneahydrate and 160 grams lead nitrate in 1500 milliliters water is added 1500 ml. of an aqueous solution containing 344 grams dibasic ammonium phosphate. The precipitate is removed by vacuum filtration, washed with water, and dried at 120°C. for 24 hours. The catalyst cake is calcined two hours at 500°C. then broken into 4–10 mesh particles. These particles are calcined at 550°C. for an additional two hours. This catalyst, which has a metal atomic ratio of 1 Fe/0.6 Pb, is placed in the reactor and heated to 450°C., and the reactants are fed thereto in accordance with the procedure described above. The following results are obtained over an 8 hour period.

| | |
|---|---|
| Conversion | = 45.0% |
| Consumption | = 65.2% |
| Yield | = 69.1% |
| Water/Isobutyric Acid | = 13.3 |
| Oxygen/Isobutyric Acid | = 0.77 |
| Contact Time | = 0.32 second |

The catalyst is regenerated by heating at 450°C. for 16 hours while passing air through the catalyst bed. After regeneration, another eight hour run is made under the conditions above with the following results.

| | |
|---|---|
| Conversion | = 45.1% |
| Consumption | = 65.3% |
| Yield | = 69.0% |

EXAMPLE 2

A catalyst is prepared according to the teaching of U.S. Pat. No. 3,634,494 to show the conversions and yields obtainable with it and its short catalytic life.

A mixture of 40.4 grams ferric nitrate enneahydrate, 97.0 grams bismuth nitrate pentahydrate, and 19.9 grams lead nitrate is dissolved in enough 1N nitric acid to make 300 milliliters solution. The salt solution is diluted to 1000 milliliters with 1N nitric acid; then, with stirring, 1000 milliliters of an aqueous solution containing 264 grams dibasic ammonium phosphate is added, effecting the precipitation of the bismuth, iron, and lead. The precipitate is removed by vacuum filtration, reslurried in 2000 milliliters water, and refiltered. The filter cake is dried overnight at 120°–140°C., broken into 4–10 mesh particles, and calcined at 550°C. for two hours. This catalyst, with a metal ratio of 2 Bi/1 Fe/0.6 Pb, is placed in the reactor, heated to 450°C., and the reactants are fed thereto in accordance with the previously described procedure. The following results are obtained over an 8 hour period.

| | |
|---|---|
| Conversion | = 34.5% |
| Consumption | = 76.0% |
| Yield | = 45.4% |
| Water/Isobutyric Acid | = 12.0 |
| Oxygen/Isobutyric Acid | = 0.71 |
| Contact Time | = 0.31 second |

At the end of this run, the conversion and yield have dropped to 29 percent and 35 percent, respectively.

The catalyst is heated to 500°C. and air passed through the bed for 16 hours. The reactor is cooled to 450°C. and another eight hour run is made with the following results.

| | |
|---|---|
| Conversion | = 29.1% |
| Consumption | = 82.2% |
| Yield | = 35.4% |

These results illustrate the failure of the catalyst to regenerate to its previous activity.

EXAMPLE 3

This example shows the superior catalytic life of the catalyst of this invention as compared to the best catalyst previously known to the art.

Samples of catalysts prepared by Examples 1 and 2 are tested in the two-stage reactor for an extended period of time. The conversion and yield for each catalyst are calculated every two hours and are shown graphically in FIG. 1. The catalyst of this invention, i.e., ferric phosphate-lead phosphate, showed no additonal loss of activity at the end of a 32 hour period.

EXAMPLE 4

In order to show the wide range of conditions in which the catalyst of this invention is operable, the water to isobutyric acid mole ratio is varied over a wide range using the catalyst of Example 1. The data thus obtained is shown graphically in FIG. 2. This data shows that the catalyst is most effective in the water to isobutyric acid mole ratio range of 8 to 12. In contrast, the catalyst of Example 2 has a maximum at a water to isobutyric acid mole ratio range of 26 to 30. This is significant in that the product from the reactor is twice as concentrated in methacrylic acid when less water is used, thus making product recovery easier and less expensive. Also, with less water, the heat load is reduced. Both factors tend to make the reaction more economical.

EXAMPLE 5

This example shows the effect of changing the composition of the ferric phosphate-lead phosphate catalyst on the activity of the catalyst.

The catalysts are prepared according to the procedure given in Example 1 except that the amount of lead nitrate and dibasic ammonium phosphate used is adjusted to obtain the desired iron to lead ratio. The maximum conversion and yield obtained with each catalyst during an eight hour run are recorded. The data obtained in this manner are shown in FIG. 3.

From the data in FIG. 3, it is apparent that optimum activity is obtained with a catalyst with an iron to lead ratio of 0.5 to 1.5.

EXAMPLE 6

This example shows the effect on the catalytic activity of compressing the catalyst of this invention into tablets of a high strength and more convenient size.

The catalyst prepared according to the procedure given in Example 1 is ground into 25–50 mesh particles after drying. These particles are tableted into ⅛ inch by ⅛ inch tablets with a crush strength of 4 kilograms and calcined at 550°C. This catalyst is placed in the reactor, heated to 450°C., and the reactants are fed thereto in accordance with the previously described procedure. The following results are obtained over an 8 hour period.

| | |
|---|---|
| Conversion | = 48.1% |
| Consumption | = 63.0% |
| Yield | = 76.4% |
| Water/Isobutyric Acid | = 12.6 |
| Oxygen/Isobutyric Acid | = 0.74 |
| Contact Time | = 0.32 second |

The improved results obtained with a tableted catalyst are quite unexpected. Generally tableted catalysts give lower conversions and yields when compared to similar catalysts in the granulated form.

EXAMPLE 7

In this example the effect of the activity of the catalyst of the presence of silica in the catalyst of this invention is shown.

The catalyst is prepared according to the procedure given in Example 1 except that 160 milliliters of a 30 percent silica colloid (Ludox AS) are added to the ferric nitrate-lead nitrate solution prior to the addition of dibasic ammonium phosphate solution. After the precipitation, the slurry is heated on the steam bath for three hours to make sure that all of the silica is precipitated. After working up the catalyst as in Example 1, the catalyst granules, with a metal ratio of 1 Fe/0.6 Pb/1 Si, are placed in the reactor, heated to 450°C., and the reactants fed thereto in accordance with the previously described procedure. The following results are obtained over an 8 hour period.

| | |
|---|---|
| Conversion | = 36.1% |
| Consumption | = 70.0% |
| Yield | = 51.7% |
| Water/Isobutyric Acid | = 13.0 |
| Oxygen/Isobutyric Acid | = 0.76 |
| Contact Time | = 0.32 second |

EXAMPLE 8

This example shows the activity of a catalyst prepared with phosphoric acid and ammonium hydroxide in place of dibasic ammonium phosphate.

Ferric nitrate enneahydrate (323 g., 0.80 mole), lead nitrate (160 g., 0.48 mole) and 85 percent phosphoric acid (300.5 g., 2.60 moles) is dissolved in enough water to make a 2300 ml. solution (pH = 0.4). Ammonium hydroxide is added with vigorous stirring until the mixture reaches a pH of 5.2. The resultant precipitate is removed by vacuum filtration, washed with 1500 ml. water and dried at 140°C. The catalyst cake is broken into 4–10 mesh particles and calcined for 2 hours at 550°C. This catalyst is utilized according to the process of Example 1. The following results are obtained over an 8 hour period.

| | |
|---|---|
| Conversion | = 44.3% |
| Consumption | = 60.3% |
| Yield | = 73.5% |
| Water/Isobutyric Acid | = 13.0 |
| Oxygen/Isobutyric Acid | = 0.80 |
| Contact Time | = 0.32 second |

Similar results are obtained from catalysts prepared by the addition of ammonium hydroxide to a solution of ferric phosphate and lead phosphate so as to bring the pH of the solution into the range of 4.0 to 7.0.

EXAMPLE 9

This example shows the activity of the catalyst of this invention in the oxidative dehydrogenation of propionic acid to acrylic acid.

The catalyst prepared by the procedure given in Example 1 is packed in the reactor, heated to 450°C., and propionic acid (40 milliliters per hour), water (100 milliliters per hour), and air are fed to the reactor. The following results are obtained over an 8 hour period.

| | |
|---|---|
| Conversion to Acrylic Acid | = 10.4% |
| Consumption | = 73.7% |
| Yield to Acrylic Acid | = 14.1% |
| Water/Propionic Acid | = 11.1 |
| Oxygen/Propionic Acid | = 0.65 |
| Contact Time | = 0.32 second |

EXAMPLE 10

This example shows the high level of activity attainable with the catalyst of this invention and the use of this catalyst in a bench-scale pilot plant unit.

The reactor for this example is made from 2-inch 316 stainless steel pipe with provisions for placing within its three catalyst beds having a total volume of 525 milliliters. The space between the catalyst beds is packed with Penn State packing and has provisions for cooling the gas stream. Air inlet points are positioned above the top bed, between the top and middle beds, and between the middle and bottom beds. Water and isobutyric acid are fed to a vaporizer-preheater and into the top of the reactor. The reactor effluent is condensed and collected. Material balances around the reactor system are made every 24 hours by analyzing a composite sample of the product stream collected during this period.

The catalyst, prepared by the procedure given in Example 7, is placed in the reactor as three equivolume beds and heated to 400°C. Isobutyric acid and water are fed to the reactor at rates of 474 grams per hour and 965 grams per hour, respectively, for an isobutyric acid to water mole ratio of 10.0 to 1. Air is fed to the reactor at rates of 1817, 2240, and 2676 milliliters per minute from the top to bottom feed points for an oxygen to isobutyric acid mole ratio of 0.7 to 1. Under these conditions, the gas streams entering each catalyst bed are adjusted to 390° ± 5°C. in order to get a 450°C. gas stream exiting each catalyst bed. The results obtained with these conditions are as follows.

|  | First Day | Second Day | Third Day | Fourth Day | Fifth Day |
| --- | --- | --- | --- | --- | --- |
| Conversion, % | 54.2 | 55.6 | 52.3 | 51.9 | 49.7 |
| Consumption, % | 61.6 | 59.7 | 56.6 | 54.7 | 58.8 |
| Yield, % | 87.9 | 93.1 | 92.4 | 94.9 | 84.5 |
| Space-Time Yield, g/MMA/liter/hr. | 478 | 492 | 462 | 459 | 438 |

Although the invention has been described in considerable detail with reference to certain preferred embodiments thereof, it will be understood that variations and modifications can be effected without departing from the spirit and scope of the invention as described hereinabove.

I claim:

1. A bismuth-free catalyst consisting essentially of the calcined residue of a mixture of ferric phosphate and lead phosphate with an atomic ratio of metal defined by 1 Fe/x Pb where x is from about 0.1 to about 10.

2. A catalyst according to claim 1 wherein x has a value of from about 0.5 to about 1.5.

3. A catalyst prepared by the steps of
   1. preparing a solution of salts of iron and lead,
   2. precipitating from said solution a mixture of ferric phosphate and lead phosphate,
   3. washing said precipitate,
   4. drying said precipitate,
   5. adjusting the size and shape of the catalyst particles to that desired for process use, and
   6. calcining said adjusted particles at a temperature of from about 400°C. to about 600°C wherein the atomic ratio of the metals is defined by 1 Fe/xPb where x is from about 0.1 to about 10.

4. A catalyst according to claim 3 wherein the solution of salts of iron and lead has a pH of from about 0.5 to about 4.0.

5. A catalyst according to claim 4 wherein the solution of salts of iron and lead has a pH of from about 2 to about 2.5.

6. A catalyst according to claim 3 wherein the pH of the solution following precipitation of ferric phosphate and lead phosphate has a pH of from about 5 to about 7.

7. A catalyst according to claim 3 wherein the precipitation of the ferric phosphate and the lead phosphate is accomplished with dibasic ammonium phosphate.

8. A catalyst according to claim 3 wherein the precipitation of ferric phosphate and lead phosphate is accomplished by the addition of ammonium hydroxide.

9. A catalyst according to claim 3 wherein the mixture of ferric phosphate and lead phosphate is precipitated from a solution of phosphoric acid, salts of iron and salts of lead.

10. A catalyst according to claim 3 wherein the mixture of ferric phosphate and lead phosphate is precipitated from an aqueous solution of phosphoric acid, salts of iron and salts of lead.

11. A catalyst according to claim 3 wherein the mixture of ferric phosphate and lead phosphate is precipitated from an aqueous solution of phosphoric acid, nitrates of iron and nitrates of lead.

12. A catalyst prepared by the steps of
    1. preparing an aqueous solution of phosphoric acid, nitrates of iron and nitrates of lead,
    2. precipitating from said solution a mixture of ferric phosphate and lead phosphate by the addition of ammonium hydroxide,
    3. washing said precipitate,
    4. drying said precipitate,
    5. adjusting the size and shape of the catalyst particles to that desired for process use, and
    6. calcining said adjusted particles at a temperature of from about 400°C. to about 600°C wherein the atomic ratio of the metals is defined by 1Fe/xPb where x is from about 0.1 to about 10.

13. A catalyst according to claim 12 wherein the pH of the solution following the precipitation of ferric phosphate and lead phosphate is from about 5.0 to about 7.0.

* * * * *